(12) United States Patent
Ogawa et al.

(10) Patent No.: US 8,796,468 B2
(45) Date of Patent: *Aug. 5, 2014

(54) ADAMANTANAMINE DERIVATIVE

(75) Inventors: Tomoyuki Ogawa, Osaka (JP); Koji Masuda, Osaka (JP)

(73) Assignee: Shionogi & Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/517,924

(22) PCT Filed: Dec. 20, 2010

(86) PCT No.: PCT/JP2010/072847
§ 371 (c)(1),
(2), (4) Date: Jun. 20, 2012

(87) PCT Pub. No.: WO2011/078101
PCT Pub. Date: Jun. 30, 2011

(65) Prior Publication Data
US 2012/0259128 A1 Oct. 11, 2012

(30) Foreign Application Priority Data

Dec. 22, 2009 (JP) ................................. 2009-290227

(51) Int. Cl.
C07C 233/36 (2006.01)
C07C 233/41 (2006.01)
C07C 271/34 (2006.01)
C07C 311/07 (2006.01)

(52) U.S. Cl.
USPC .............. 548/369.7; 548/374.1; 560/115; 564/98; 564/217

(58) Field of Classification Search
None
See application file for complete search history.

(56) References Cited

U.S. PATENT DOCUMENTS

| | | | |
|---|---|---|---|
| 6,166,063 A | 12/2000 | Villhauer | |
| 7,728,029 B2 | 6/2010 | Anderson et al. | |
| 2006/0079506 A1 | 4/2006 | Linders et al. | |
| 2008/0096869 A1 | 4/2008 | Linders et al. | |
| 2009/0170832 A1 | 7/2009 | Kurose et al. | |
| 2010/0105923 A1 | 4/2010 | Watanabe | |
| 2010/0240659 A1 | 9/2010 | Masuda et al. | |
| 2011/0009391 A1 | 1/2011 | Braun et al. | |
| 2011/0086405 A1 | 4/2011 | Tomikawa et al. | |
| 2011/0159019 A1 | 6/2011 | Tanaka et al. | |
| 2011/0269971 A1 | 11/2011 | Watanabe | |
| 2013/0197240 A1* | 8/2013 | Nishino et al. | 548/374.1 |

FOREIGN PATENT DOCUMENTS

| | | |
|---|---|---|
| EP | 2088136 | 8/2009 |
| EP | 2221380 | 8/2010 |
| EP | 2345640 | 7/2011 |
| EP | 2518051 | 10/2012 |
| WO | 00/34241 | 6/2000 |
| WO | 2005/016877 | 2/2005 |
| WO | 2007/114125 | 10/2007 |
| WO | 2009/068531 | 6/2009 |
| WO | 2011/012800 | 2/2011 |
| WO | 2012/124781 | 9/2012 |

OTHER PUBLICATIONS

Lavrova et al., "Some amino alcohols of the adamantane series and their derivatives," translated from Zhurnal Organicheskoi Khimii, 1976, vol. 12, No. 11, pp. 2369-2374.

Klimova et al., "Hydroxyaminoadamantanes and their biological activity," Khimiko Farmatsevticheskii Zhurnal, 1986, vol. 20, No. 7, pp. 810-815, with English abstract.

Jaroskova et al., "An expeditious preparation of E-2-amino-5-hydroxyadamantane and its Z-isomer," Tetrahedron Letters, 2006, vol. 47, pp. 8063-8067.

Van Deursen et al., "Origin of anomalous shift additivity in rigid saturated molecules: NMR spectra of secondary substituted adamantanes, part III," Tetrahedron, 1971, vol. 27, issue 19, pp. 4593-4600.

Villhauer et al., "1-[[(3-hydroxy-l-admantyl)amino]acetyle]-2-cyano-(S)-pyrrolidine: a potent, selective, and orally bioavailable dipeptidyl peptidase IV inhibitor with antihyperglycimic properties," Journal of Medicinal Chemistry, 2003, vol. 46, No. 13, pp. 2774-2789.

* cited by examiner

*Primary Examiner* — Kamal Saeed
(74) *Attorney, Agent, or Firm* — Hamre, Schumann, Mueller & Larson, P.C.

(57) ABSTRACT

Disclosed is an adamantanamine derivative which is useful as a significant intermediate of an 11βHSD-1 inhibitor.
Disclosed is a compound represented by the formula (II):

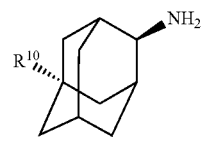

(II)

wherein $R^{10}$ is a group represented by the formula: $-(CR^{13}R^{14})m-NR^{12}-R^{11}$ or the like.

9 Claims, No Drawings

ADAMANTANAMINE DERIVATIVE

FIELD OF THE INVENTION

The present invention relates to an adamantanamine derivative. In detail, the present invention relates to an adamantanamine derivative useful as a significant intermediate of an 11βHSD-1 inhibitor (11β-hydroxysteroid dehydrogenase type 1 inhibitor) and a process for producing an 11βHSD-1 inhibitor using the above derivative.

BACKGROUND ART

A compound represented by the formula (III):

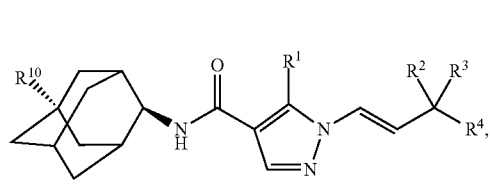

its salt, or a solvate thereof is known to show an inhibitory activity to 11βHSD-1. A pharmaceutical composition comprising the compound is also known to be useful as a medicament for treatment of type II diabetes (Patent Document 1 or Patent Document 2).

Example 69 of Patent Document 1 discloses the following process for producing the above compound.

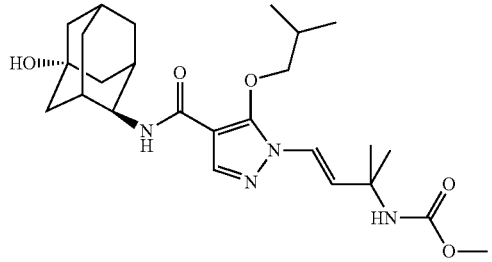

Example 1 of Patent Document 2 discloses the following process for producing the above compound.

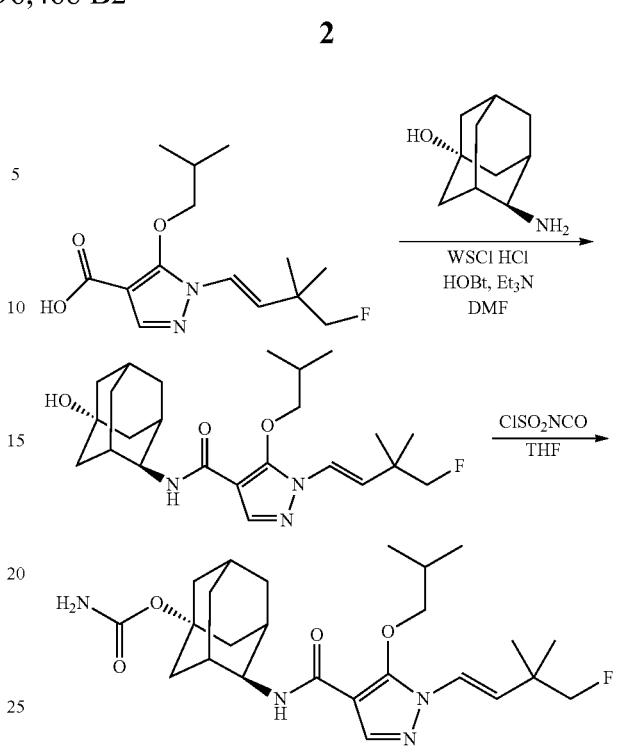

Example 84 of Patent Document 2 discloses the following process.

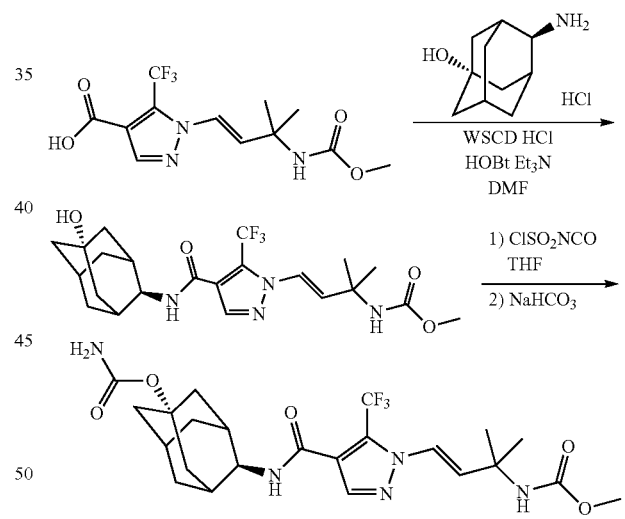

Moreover, Patent Document 3 discloses a compound represented by the formula:

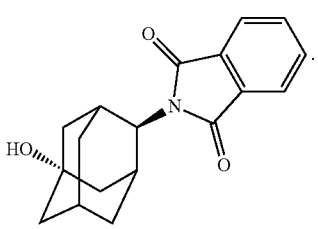 [SMILES: O=C1c2ccccc2C(=O)N1[C@H]1C2CC3CC1C[C@](O)(C3)C2]

The intermediate of the present invention and the process for producing the compound represented by the formula (III) using the intermediate have not been disclosed in any documents.

PRIOR ART DOCUMENT

Patent Document

[Patent Document 1] WO2007/058346
[Patent Document 2] WO2008/142986
[Patent Document 3] WO2007/114125

DISCLOSURE OF INVENTION

Problems to be Solved by the Invention

The present invention provides a useful intermediate for effectively producing the compound represented by the formula (III):

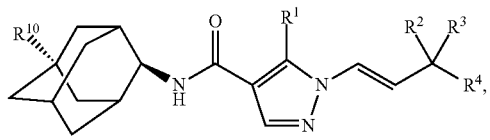

its salt, or a solvate thereof. Moreover, the present invention provides a process for producing the compound represented by the formula (III), its salt, or a solvate thereof using the intermediate.

Means for Solving the Problem

The present inventors have found that a compound represented by the formula (II):

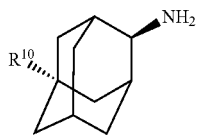

is useful as an intermediate for producing a compound represented by the formula (III). The compound represented by the formula (III) can be produced effectively by using the intermediate of the present invention.

The prior art describes the method for modifying hydroxy group on adamantane after the production of a compound represented by the formula (V):

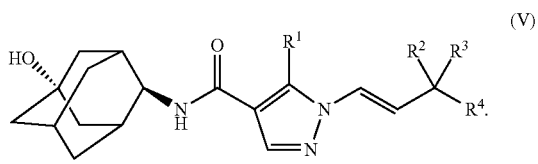

This method requires the use of the compound represented by the formula (V) as a starting material, although the compound is prepared through many steps. Therefore, this method is not economical when the yield of the subsequent modification reaction is low or the number of steps to the desired product is large.

The present inventors have found that the compound represented by the formula (III) can be produced effectively at first by preparing an adamantanamine derivative having a desired substituent, then reacting the adamantanamine derivative with a compound represented by the formula (I):

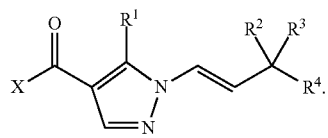

The present invention includes:

(1)

A compound represented by the formula (II):

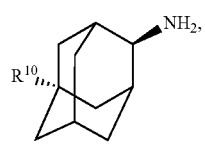

its salt, or a solvate thereof,
wherein $R^{10}$ is a group represented by the formula: $-(CR^{13}R^{14})m-NR^{12}-R^{11}$, wherein $R^{11}$ is substituted or unsubstituted acyl, substituted or unsubstituted alkylsulfonyl, substituted or unsubstituted alkyloxycarbonyl, substituted or unsubstituted carbamoyl or substituted or unsubstituted sulfamoyl, $R^{12}$ is hydrogen or substituted or unsubstituted alkyl, $R^{13}$ and $R^{14}$ are each independently hydrogen, substituted or unsubstituted alkyl or halogen, m is an integer of 0 to 3 or a group represented by the formula: $-(CR^{13}R^{14})m-O-C(O)-NR^{15}-R^{16}$, wherein $R^{15}$ and $R^{16}$ are each independently hydrogen or substituted or unsubstituted alkyl, $R^{13}$, $R^{14}$ and m are as defined above.

(2)

The compound according to the above (1), its salt, or a solvate thereof, wherein m is 0.

(3)

The compound according to the above (1) or (2), its salt, or a solvate thereof, wherein $R^{10}$ is a group represented by the formula: $-(CR^{13}R^{14})m-O-C(O)-NR^{15}-R^{16}$.

(4)

The compound according to the above (1) or (2), its salt, or a solvate thereof, wherein $R^{10}$ is a group represented by the formula: $-(CR^{13}R^{14})m-NR^{12}-R^{11}$.

(5)

A process for producing a compound represented by the formula (III):

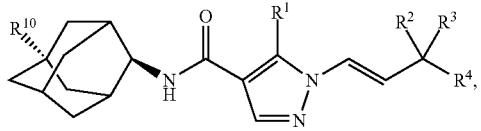

its salt, or a solvate thereof,
wherein

R¹ is a group represented by the formula: —Y—R⁵,
wherein Y is a bond, —O— or —S—, R⁵ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocyclyl, R² and R³ are each independently hydrogen, substituted or unsubstituted alkyl or halogen, or R² and R³ taken together with the adjacent carbon atom to which they are attached may form a substituted or unsubstituted ring, R⁴ is a group represented by the formula: —C(=O)—NR⁶R⁷,
wherein R⁶ and R⁷ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl or substituted or unsubstituted heterocyclylsulfonyl, or R⁶ and R⁷ taken together with the adjacent nitrogen atom to which they are attached may form a substituted or unsubstituted ring or a group represented by the formula: —NR⁸R⁹,
wherein R⁸ and R⁹ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted sulfamoyl, or R⁸ and R⁹ taken together with the adjacent nitrogen atom to which they are attached may form a substituted or unsubstituted ring, R¹⁰ is as defined in the above (1),
which comprises reacting a compound represented by the formula (I):

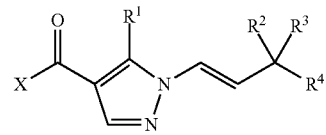

wherein R¹, R², R³ and R⁴ are as defined above, X is hydroxy or a leaving group, and a compound represented by the formula (II):

wherein R¹⁰ is as defined in the above (1).

(6)

The process according to the above (5), wherein X is hydroxy and the reaction is performed in the presence of a condensing agent.

(7)

The process according to the above (6), wherein the condensing agent is one or more condensing agent(s) selected from N,N'-dicyclohexylcarbodiimide, N,N'-diisopropylcarbodiimide and 1-ethyl-3-(3-dimethylamino propyl)carbodiimide hydrochloride.

(8)

The process according to the above (6) or (7), wherein the reaction is performed in the presence of one or more additive agent(s) selected from 1-hydroxybenzotriazole and N-hydroxy succinimide.

(9)

The process according to the above (5), which includes a step of obtaining the compound represented by the formula (I):

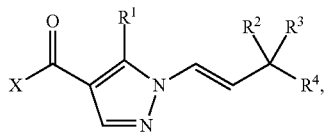

its salt, or a solvate thereof,
wherein

X is halogen, R¹, R², R³ and R⁴ are as defined in the above (5) which comprises reacting a compound represented by the formula (IV):

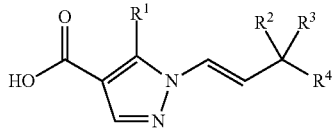

(IV)

wherein $R^1$, $R^2$, $R^3$ and $R^4$ are as defined in the above (5) with a halogenating agent.

(10)

The process according to the above (9), wherein the halogenating agent is selected from phosphorus oxychloride, phosphorus pentachloride, oxalyl chloride and thionyl chloride.

(11)

The process according to any one of the above (5) to (10), which comprises reacting a compound represented by the formula (I) with a compound represented by the formula (II) in the presence of a base.

In this specification, reacting a compound with a compound includes reacting a compound, its salt, or a solvate thereof with a compound, its salt, or a solvate thereof.

Effect of the Invention

The compound represented by the formula (II) is useful as an intermediate for producing the compound represented by the formula (III). The compound represented by the formula (III) can be produced effectively by using the intermediate of the present invention.

MODE FOR CARRYING OUT THE INVENTION

The compound represented by the formula (II):

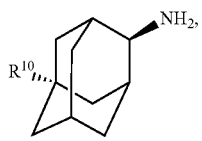

(II)

wherein $R^{10}$ is a group represented by the formula: —$(CR^{13}R^{14})_m$-$NR^{12}$—$R^{11}$, wherein $R^{11}$ is substituted or unsubstituted acyl, substituted or unsubstituted alkylsulfonyl, substituted or unsubstituted alkyloxycarbonyl, substituted or unsubstituted carbamoyl or substituted or unsubstituted sulfamoyl, $R^{12}$ is hydrogen or substituted or unsubstituted alkyl, $R^{13}$ and $R^{14}$ are each independently hydrogen, substituted or unsubstituted alkyl or halogen, m is an integer of 0 to 3 or a group represented by the formula: —$(CR^{13}R^{14})_m$-O—C(O)—$NR^{15}$—$R^{16}$, wherein $R^{15}$ and $R^{16}$ are each independently hydrogen or substituted or unsubstituted alkyl, $R^{13}$, $R^{14}$ and m are as defined above, can be prepared by the following method.

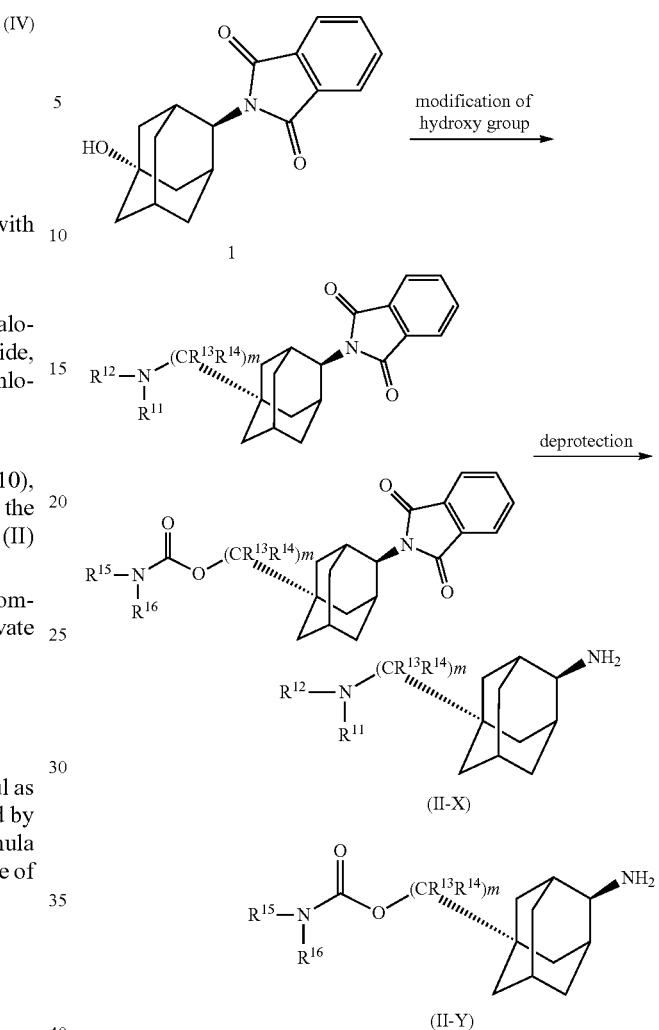

wherein a compound represented by the formula (II-X) and a compound represented by the formula (II-Y) in the above scheme are concrete examples of a compound represented by the formula (II).

Compound 1 is disclosed in WO2007/114125.

A compound represented by the formula (II-X) and a compound represented by the formula (II-Y) can be prepared by using Compound 1 as a starting material, modifying a hydroxy group of the Compound 1, then deprotecting an amino protecting group (phthalimido group).

For example, the compound represented by the formula (II) wherein $R^{11}$ is substituted or unsubstituted alkylsulfonyl can be prepared by reacting Compound 1 with a nitriles in the presence of concentrated sulfuric acid.

The compound represented by the formula (II) wherein $R^{15}$ and $R^{16}$ are each independently hydrogen or substituted or unsubstituted alkyl can be prepared by reacting Compound 1 with an amine in the presence of carbonyldiimidazole.

Moreover, the compound represented by the formula (II) wherein $R^{15}$ and $R^{16}$ are hydrogen or one of $R^{15}$ and $R^{16}$ is hydrogen and the other of $R^{15}$ and $R^{16}$ is substituted or unsubstituted alkyl can be prepared by reacting Compound 1 with various isocyanates.

Moreover, the compound represented by the formula (II) can be prepared by preparing Compound 5:

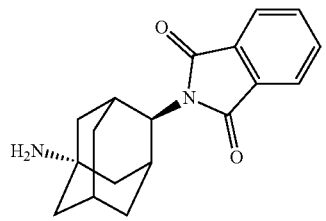

from Compound 1 according to the method described in Example 3, modifying a free amino group to produce various amino derivative, then deprotecting a phthalimido group of the amino derivative.

For example, the compound represented by the formula (II) wherein $R^{11}$ is substituted or unsubstituted acyl can be prepared by reacting Compound 5 with various acyl halides, then deprotecting a phthalimido group.

For example the compound represented by the formula (II) wherein $R^{11}$ is substituted or unsubstituted alkylsulfonyl can be prepared by reacting Compound 5 with various sulfonyl halides (ex. alkylsulfonyl halide.), then deprotecting a phthalimido group.

The compound represented by the formula (II) wherein $R^{11}$ is substituted or unsubstituted alkyloxycarbonyl can be prepared by reacting Compound 5 with various alkyloxycarbonyl halides (ex. methyl chlorocarbonate.), then deprotecting a phthalimido group.

In addition of the above example, other compounds represented by the formula (II) can be prepared from Compound 1 by common organic chemical reactions.

Hydrazine, methylhydrazine or the like can be used for deprotection of phthalimide group. Alcohols can be used as a solvent. The above deprotection step can be performed under reflux.

The compound wherein m is 1 can be prepared by the following method.

The compound represented by the formula (II) wherein m is 1 can be prepared by converting hydroxy group to carboxy group by reacting Compound 1 with 30% fuming sulfuric acid and formic acid, converting to methyl ester derivative by reacting the obtained compound with acetyl chloride or the like in methanol, converting ester to hydroxymethyl derivative by reduction with lithium borohydride or the like, conducting various modification of the hydroxymethyl derivative, then conducting chemical reaction in accordance with the case that m=0.

For example, a carbamoyloxymethyl derivative can be prepared by reacting the hydroxymethyl derivative with a chlorosulfonyl isocyanate, then deprotecting a phthalimido group.

The compound wherein m is 2 can be prepared by the following method.

The compound represented by the formula (II) wherein m is 2 can be prepared by converting hydroxymethyl group of the above hydroxymethyl derivative to —$CH_2X$ (X is a leaving group such as halogen, Ms or Ts.), converting —$CH_2X$ to —$CH_2CN$ by treating the obtained compound with KCN or NaCN, converting —$CH_2CN$ to —$CH_2CO_2H$ by hydrolysis, converting to —$CH_2CH_2OH$ by reduction, then conducting chemical reactions in accordance with the case that m=0.

The compound wherein m is 3 can be prepared by the following method.

A compound represented by the formula (II) wherein m is 3 can be produced by converting the above —$CH_2CH_2OH$ to —$CH_2CH_2CH_2OH$ by the above method, then conducting chemical reaction in accordance with the case that m=0.

A compound represented by the formula (III) can be prepared using the compound represented by the formula (II) prepared in accordance with the above method.

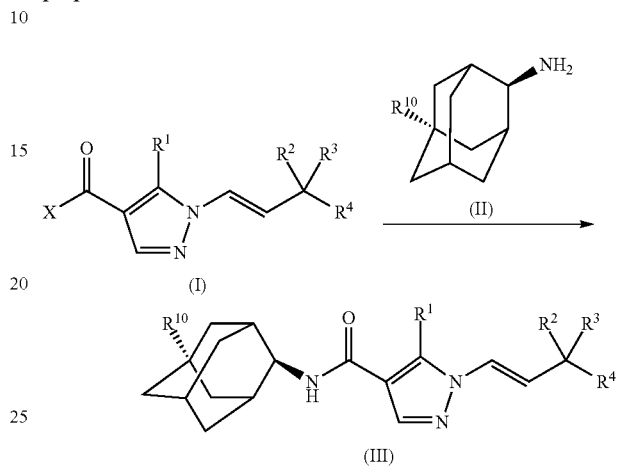

wherein $R^1$ is a group represented by the formula: —Y—$R^5$, wherein Y is a bond, —O— or —S—, $R^5$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocyclyl, $R^2$ and $R^3$ are each independently hydrogen, substituted or unsubstituted alkyl or halogen, $R^2$ and $R^3$ taken together with the adjacent carbon atom to which they are attached may form a substituted or unsubstituted ring, $R^4$ is a group represented by the formula: —C(=O)—$NR^6R^7$, wherein $R^6$ and $R^7$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl or substituted or unsubstituted heterocyclylsulfonyl, $R^6$ and $R^7$ taken together with the adjacent nitrogen atom to which they are attached may form a substituted or unsubstituted ring or a group represented by the formula: —$NR^8R^9$, wherein $R^8$ and $R^9$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl or substituted or unsubstituted sulfamoyl, $R^8$ and $R^9$ taken together with the adjacent nitrogen atom to which they are attached may form a substituted or unsubstituted ring, X is hydroxy or a leaving group, $R^{10}$ is a group represented by the formula: —$(CR^{13}R^{14})$m-$NR^{12}$—$R^{11}$, wherein $R^{11}$ is substituted or unsubstituted acyl, substituted or unsubstituted alkylsulfonyl, substituted or unsubstituted alkyloxycarbonyl, substituted or unsubstituted carbamoyl or substituted or unsubstituted sulfamoyl, $R^{12}$ is hydrogen or substituted or unsubstituted alkyl, $R^{13}$ and $R^{14}$ are each independently hydrogen, substituted or unsubstituted alkyl or halogen, m is an integer of 0 to 3 or a group represented by the formula: —$(CR^{13}R^{14})$m-O—C(O)—$N(R^{15}R^{16})$, wherein $R^{15}$ and $R^{16}$ are each independently hydrogen or substituted or unsubstituted alkyl, $R^{13}$, $R^{14}$ and m are as defined above.

This step is a process for preparing the compound represented by the formula (III) which comprises reacting the compound represented by the formula (I) with the compound represented by the formula (II).

The process can be performed in the presence of a condensing agent when X is hydroxy.

An amide condensing agent commonly used in a condensation reaction between carboxy group and amino group can be used as a condensing agent. As a condensing agent, example includes carbodiimides (e.g., N,N'-dicyclohexylcarbodiimide, N,N'-diisopropyl carbodiimide, 1-ethyl-3-(3-dimethylaminopropyl)carbodiimide hydrochloride or the like), diphenylphosphoryl azide, BOP reagent (e.g., BOP, PyBop, TBTU or the like), DMT-MM, 1,1'-carbonylbis-1H-imidazole, 2-chloro-1,3-dimethylimidazolium chloride, 4-(4,6-dimethoxy-1,3,5-triazine-2-yl)-4-methylmorpholinium chloride or the like. Preferable is N,N'-dicyclohexylcarbodiimide, N,N'-diisopropyl carbodiimide or 1-ethyl-3-(3-dimethylaminopropyl)carbodiimide hydrochloride. Especially, preferable is 1-ethyl-3-(3-dimethylaminopropyl)carbodiimide hydrochloride.

The process can be performed in the presence of an additive agent.

An example of an additive agent includes 1-hydroxybenzotriazole, N-hydroxy succinimide or the like. Especially, preferable is 1-hydroxybenzotriazole.

The process can be performed in the presence of a base. The base can be appropriately selected according to the kind of a leaving group or a solvent.

An example of a base includes organic bases such as triethylamine, diisopropylethylamine, pyridine, imidazole or diazabicycloundecene. Preferable is triethylamine, diisopropylethylamine, diazabicycloundecene or the like. Especially, preferable is triethylamine.

The process can be performed at −20 to 200° C., preferably at 0 to 100° C.

An example of a solvent includes water, alcohols such as methanol, ethanol or propanol, halogenated hydrocarbons such as dichloromethane or chloroform, aromatic hydrocarbons such as benzene, toluene or xylene, aprotic polar solvent such as dimethylformamide, dimethylacetamide or 1-methyl-2-pyrolidone, ethers such as tetrahydrofuran or dioxane, acetonitrile or the like. Especially, preferable is dichloromethane or dimethylformamide.

A salt or a solvate of the compound represented by the formula (I) or the compound represented by the formula (II) can be used.

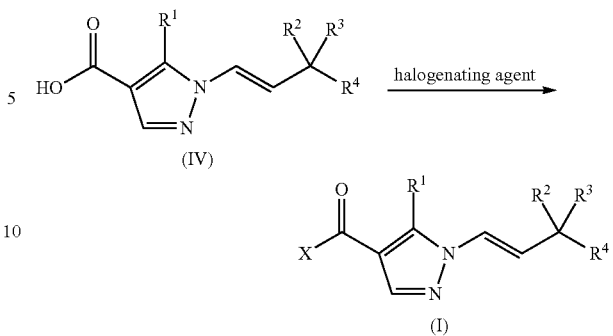

wherein X is halogen, each symbol has the same meaning as the above in the above scheme.

This step is a process for preparing the compound represented by the formula (I) which comprises reacting the compound represented by the formula (IV) with a halogenating agent.

An example of a halogenating agent includes thionyl chloride, thionyl bromide, oxalyl chloride, phosphorus oxychloride, phosphorus trichloride, phosphorus pentachloride, phosphorus tribromide or the like. Preferable is thionyl chloride, thionyl bromide, oxalyl chloride or phosphorus oxychloride. Especially, preferable is thionyl chloride.

The process can be performed at 0 to 100° C., preferably at 20 to 60° C.

An example of a solvent includes tetrahydrofuran, ethyl acetate, dimethylformamide or the like. Especially, preferable is tetrahydrofuran.

After the completion of this process, the compound represented by the formula (III) can be produced by reacting the isolated or non-isolated compound represented by the formula (I) with the compound represented by the formula (II).

A salt or a solvate of the compound represented by the formula (IV) can be used.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group or a fused aromatic heterocyclic group. The monocyclic aromatic heterocyclic group means a group derived from a 5- to 8-membered aromatic ring which may contain 1 to 4 oxygen, sulfur and/or nitrogen atom(s) in the ring, and may have a bond at a substitutable arbitrary position.

The fused aromatic heterocyclic group means a group in which a 5- to 8-membered aromatic ring optionally containing 1 to 4 oxygen, sulfur and/or nitrogen atom(s) in the ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), benzothiazolyl, dibenzofuryl, benzoxazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-cinnolinyl), quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Cycloalkyl" means a C3 to C15 cyclic saturated hydrocarbon group, and example includes cyclopropyl, cyclobutyl, cyclopentyl, cyclohexyl, cycloheptyl, cyclooctyl or the like. Preferable is cyclopropyl, cyclobutyl, cyclopentyl or cyclohexyl.

"Cycloalkenyl" means C3 to C15 cyclic unsaturated aliphatic hydrocarbon group, and example includes cyclopropenyl, cyclobutenyl, cyclopentenyl, cyclohexenyl or cycloheptenyl. Preferable is cyclopropenyl, cyclobutenyl, cyclopentenyl or cyclohexenyl.

"Heterocyclyl" means a nonaromatic heterocyclic group which may contain 1 to 4 oxygen, sulfur and/or nitrogen atom(s) in the ring, and may have a bond at a substitutable arbitrary position. Moreover, the nonaromatic heterocyclic group can be bridged with a C1 to C4 alkyl chain, or can be fused with cycloalkane (5- to 6-membered ring is preferable) or benzene ring. "Nonaromatic heterocyclic group" can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl.

"Halogen" includes fluorine, chlorine, bromine or iodine. Especially, preferable is chlorine, bromine or iodine.

"A saturated or unsaturated ring formed by taking together with the adjacent carbon atom to which they are attached" means a 3- to 8-membered ring. Preferable is a 4- to 6-membered ring. The ring may contain heteroatom(s) (oxygen, sulfur, and/or nitrogen atom(s)) besides the above carbon atom in the ring.

"A saturated or unsaturated ring formed by taking together with the adjacent nitrogen atom to which they are attached" means a 3- to 8-membered ring. Preferable is a 4- to 6-membered ring. The ring may contain carbon atom(s) and more heteroatom(s) (oxygen, sulfur, and/or nitrogen atom(s)) besides the above nitrogen atom in the ring.

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl.

The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl" and the heterocyclyl part of "heterocyclylcarbonyl" respectively mean the above "alkyl", the above "alkenyl", the above "cycloalkyl", the above "cycloalkenyl", the above "aryl", the above "heteroaryl" and the above "heterocyclyl".

"a leaving group" includes alkyloxy, aryloxy, acyloxy, alkoxycarbonyloxy, arylcarbonyloxy, alkylsulfonyloxy, halogen or the like. Especially, preferable is halogen.

The alkyl part of "alkylsulfonyl", the aryl part of "arylsulfonyl", the heteroaryl part of "heteroarylsulfonyl", the heterocyclyl part of "heterocyclylsulfonyl" and the alkyl part of "alkyloxycarbonyl" respectively mean the above "alkyl", the above "aryl", the above "heteroaryl" and the above "heterocyclyl".

"Substituted alkyl", "substituted alkenyl", "substituted alkynyl", "substituted aryl", "substituted heteroaryl", "substituted cycloalkyl", "substituted cycloalkenyl", "substituted heterocyclyl", "a ring formed by taking together with the adjacent carbon atom to which they are attached", "substituted amino", "substituted alkylsulfonyl", "substituted arylsulfonyl", "substituted heteroarylsulfonyl", "substituted heterocyclylsulfonyl", "a ring formed by taking together with the adjacent nitrogen atom to which they are attached", "substituted acyl", "substituted carbamoyl", "substituted thiocarbamoyl", "substituted alkyloxycarbonyl", "substituted sulfamoyl", "substituted alkylcarbonyl", "substituted alkenylcarbonyl", "substituted cycloalkylcarbonyl", "substituted cycloalkenylcarbonyl", "substituted arylcarbonyl", "substituted heteroarylcarbonyl" and "substituted heterocyclylcarbonyl"

may be substituted with 1 to 4 substituent(s) selected from a group consisting of, for example, halogen, hydroxy, carboxy, nitro, cyano, substituted or unsubstituted alkyl (an example of a substituent of substituted alkyl includes halogen, hydroxy, carboxy, cyano, amino, alkyl, aryl, cycloalkyl, heteroaryl, heterocyclyl, alkyloxycarbonyl, alkyloxycarbonylamino or carbamoyl. e.g.: methyl, ethyl, isopropyl, tert-butyl, $CF_3$, $CH_2OH$, $CH_2CH_2OH$, $CH_2COOCH_3$, $CH_2NH_2$, $CH_2CN$ or benzyl), substituted or unsubstituted alkenyl (an example of a substituent of substituted alkenyl includes halogen, carboxy, alkyl, aryl, cycloalkyl, heteroaryl or heterocyclyl. e.g.: vinyl), substituted or unsubstituted alkynyl (an example of a substituent of substituted alkynyl includes halogen, alkyl, aryl, cycloalkyl, heteroaryl or heterocyclyl. e.g.: ethynyl), substituted or unsubstituted aryl (an example of a substituent of substituted aryl includes halogen, alkyl, aryl, cycloalkyl, heteroaryl, heterocyclyl or substituted or unsubstituted heterocyclyloxy. e.g.: phenyl or naphthyl), substituted or unsubstituted cycloalkyl (an example of a substituent of substituted cycloalkyl includes halogen, cyano, alkyl, aryl, cycloalkyl, heteroaryl, heterocyclyl or alkyloxycarbonyl. e.g.: cyclopropyl or cyclobutyl), substituted or unsubstituted cycloalkenyl (an example of a substituent of substituted cycloalkenyl includes halogen, alkyl, aryl, cycloalkyl, heteroaryl or heterocyclyl. e.g.: cyclopropenyl), substituted or unsubstituted heteroaryl (an example of a substituent of substituted heteroaryl includes halogen, alkyl, aryl, cycloalkyl, heteroaryl or heterocyclyl. e.g.: tetrazolyl, indolyl or pyrazolyl), substituted or unsubstituted heterocyclyl (an example of a substituent of substituted heterocyclyl includes halogen, alkyl, aryl, cycloalkyl, heteroaryl or heterocyclyl. e.g.: pyrrolidinyl, morpholinyl, piperazinyl or piperidyl), substituted or unsubstituted alkyloxy (an example of a substituent of substituted alkyloxy includes halogen, carboxy, cyano, alkyl, aryl, cycloalkyl, heteroaryl or heterocyclyl. e.g.: methoxy, ethoxy, propoxy, butoxy or $OCF_3$), substituted or unsubstituted aryloxy (an example of a substituent of substituted aryloxy includes halogen, alkyl, aryl, cycloalkyl, heteroaryl or heterocyclyl. e.g.: phenyloxy), substituted or unsubstituted silyloxy, substituted or unsubstituted amino (e.g.: alkylamino (e.g.: methylamino, ethylamino or dimethylamino), acylamino (e.g.: acetylamino or benzoylamino), arylalkylamino (e.g.: benzylamino or tritylamino), hydroxyamino, alkylaminoalkyl (e.g.: diethylaminomethyl), alkyloxycarbonylamino, alkylsulfonylamino, carbamoylamino, heterocyclylcarbonylamino, arylsulfonylamino, heteroarylsulfonylamino), substituted or unsubstituted carbamoyl (an example of a substituent of substituted carbamoyl includes hydroxy, cyano, substituted or unsubstituted alkyl, alkyloxy or alkylsulfonyl. e.g.: alkylcarbamoyl (e.g.: methylcarbamoyl, ethylcarbamoyl, dimethylcarbamoyl, phenylethylcarbamoyl, dimethylaminoethylcarbamoyl, isopropylcarbamoyl or hydroxyethylcarbamoyl), alkylsulfonylcarbamoyl, heteroarylalkylcarbamoyl or substituted or unsubstituted alkyloxycarbamoyl), substituted or unsubstituted carbamoyloxy (an example of a substituent of substituted carbamoyloxy includes halogen, alkyl, aryl, cycloalkyl, heteroaryl or heterocyclyl.), substituted or unsubstituted acyl (an example of a substituent of substituted acyl includes halogen, alkyl, aryl, cycloalkyl, heteroaryl or heterocyclyl. e.g.: alkylcarbonyl, arylcarbonyl, heteroarylcarbonyl, heterocyclylcarbonyl, formyl or acetyl), substituted or unsubstituted alkylsulfonyl (an example of a substituent of substituted alkylsulfonyl includes halogen, alkyl, aryl, cycloalkyl, heteroaryl or heterocyclyl. e.g.: methanesulfonyl or ethanesulfonyl), substituted or unsubstituted arylsulfonyl, substituted or unsubstituted heteroarylsulfonyl (an example of a substituent of substituted heteroarylsulfonyl includes halogen, alkyl, aryl, cycloalkyl, heteroaryl or heterocyclyl.), substituted or unsubstituted sulfamoyl, substituted or unsubstituted alkyloxycarbonyl (an example of a substituent of substituted alkyloxycarbonyl includes halogen, alkyl, aryl, cycloalkyl, heteroaryl or heterocyclyl. e.g.: methoxycarbonyl, ethoxycarbonyl or tert-butoxycarbonyl), aryloxycarbonyl, heteroaryloxycarbonyl, heterocyclyloxycarbonyl, cycloalkylsulfonyl, heteroarylsulfonyl, heterocyclylsulfonyl, alkylsulfinyl, cycloalkylsulfinyl, arylsulfinyl, heteroarylsulfinyl, heterocyclylsulfinyl, nitroso, alkenyloxy (e.g.: vinyloxy or allyloxy), arylalkyloxy (e.g.: benzyloxy), azide, isocyano, isocyanato, thiocyanato, isothiocyanato, mercapto, alkylthio (e.g.: methylthio), formyloxy, haloformyl, oxalo, thioformyl, thiocarboxy, dithiocarboxy, thiocarbamoyl, sulfino, sulfo, sulfoamino, hydrazino, ureide, amidino, guanidino, phthalimide, oxo and the like.

One or more hydrogen, carbon or other atoms of the compound of the present invention can be replaced by an isotope of the hydrogen, carbon or other atoms.

For example, compounds of formula (II) include all radiolabeled forms of compounds of formula (II). The "radiolabeled," "radiolabeled form" and the like of the compound of formula (II) are encompassed by the present invention and useful as a research and/or diagnostic tool in metabolism pharmacokinetic studies and in binding assays.

Examples of isotopes that can be incorporated into the compound of formula (II) of the present invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Radiolabeled compounds of the present invention can be prepared by methods known in the art. For example, tritiated compounds of formula (II) can be prepared by introducing tritium into the particular compound of formula (II), for example, by catalytic dehalogenation with tritium. This method may include reacting a suitably halogen-substituted precursor of a compound of formula (II) with tritium gas in the presence of a suitable catalyst such as Pd/C, in the presence or absence of a base. Other suitable methods for preparing tritiated compounds can be found in *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

The following salts can be included as a salt of the present compound.

An example of a basic salt includes alkali metal salt such as sodium salt or potassium salt; alkaline earth metal salt such as calcium salt or strontium salt; metal salt such as beryllium salt, magnesium salt, zinc salt or transition metal salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

An example of an acidic salt includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

The term "solvate" means a solvate of a compound of the present invention or a salt thereof, and example includes alcohol (e.g., ethanol) solvate, hydrate or the like. Example of hydrate includes monohydrate, dihydrate or the like.

$R^{10}$ is a group represented by the formula: —$(CR^{13}R^{14})$m-$NR^{12}$—$R^{11}$ or a group represented by the formula: —$(CR^{13}R^{14})$m-O—$C(O)$—$NR^{15}$—$R^{16}$.

$R^{11}$ is substituted or unsubstituted acyl, substituted or unsubstituted alkylsulfonyl, substituted or unsubstituted alkyloxycarbonyl, substituted or unsubstituted carbamoyl or substituted or unsubstituted sulfamoyl. Preferable is substituted or unsubstituted acyl, substituted or unsubstituted alkylsulfonyl or substituted or unsubstituted alkyloxycarbonyl.

$R^{12}$ is hydrogen or substituted or unsubstituted alkyl. Preferable is hydrogen.

$R^{13}$ and $R^{14}$ are each independently hydrogen, substituted or unsubstituted alkyl or halogen. Preferable is hydrogen.

$R^{15}$ and $R^{16}$ are each independently hydrogen or substituted or unsubstituted alkyl.

m is an integer of 0 to 3. Preferable is 0 or 1. Especially, preferable is 0.

$R^1$ is a group represented by the formula: —Y—$R^5$.

Y is a bond, —O— or —S—. Preferable is —O—.

$R^5$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocyclyl. Preferable is substituted or unsubstituted alkyl.

$R^2$ and $R^3$ are each independently hydrogen, substituted or unsubstituted alkyl or halogen, $R^2$ and $R^3$ taken together with the adjacent carbon atom to which they are attached may form a substituted or unsubstituted ring. As $R^2$ and $R^3$, preferable is substituted or unsubstituted alkyl.

$R^4$ is a group represented by the formula: —$C(=O)$—$NR^6R^7$ or a group represented by the formula: —$NR^8R^9$. Preferable is a group represented by the formula: —$NR^8R^9$.

$R^6$ and $R^7$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl or substituted or unsubstituted heterocyclylsulfonyl, $R^6$ and $R^7$ taken together with the adjacent nitrogen atom to which they are attached may form a substituted or unsubstituted ring. As $R^6$ and $R^7$, preferable is hydrogen.

$R^8$ and $R^9$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl or substituted or unsubstituted sulfamoyl, $R^8$ and $R^9$ taken together with the adjacent nitrogen atom to which they are attached may form a substituted or unsubstituted ring. As $R^8$ and $R^9$, preferable is hydrogen, substituted or unsubstituted alkyloxycarbonyl or substituted or unsubstituted acyl.

X is hydroxy or a leaving group.

A compound represented by the formula (II) is preferably the following compound.

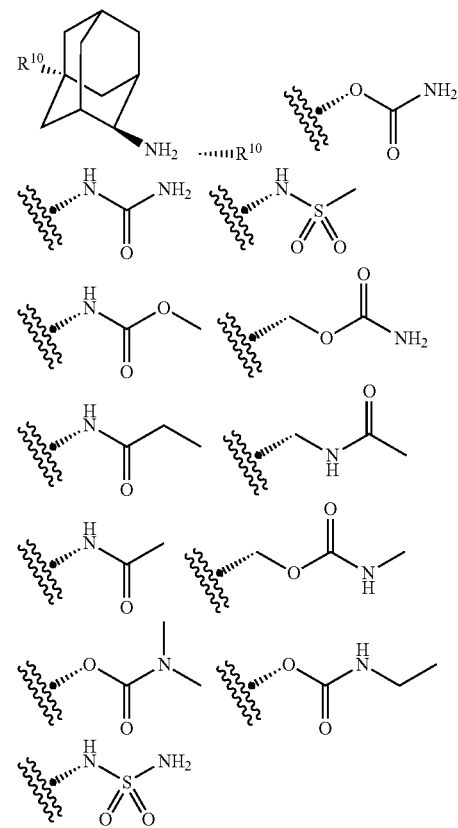

The present invention is further explained by the following Examples, which are not intended to limit the scope of the present invention.

The measurement results of NMR or log k' of the present compounds were described below.

log k' is a value which means degree of the lipophilic character, and is calculated by the following formula.

$$\log k' = \log(t_R - t_0)/t_0$$

$t_R$: retention time of compound under gradient condition
$t_0$: retention time of standard material not retained in column XTerra MS C18 5 μm, 2.1×100 mm column (made by Waters) was used for measurement. The elution was a straight line inclination of acetonitrile/pH6.8 buffer (5:95~95:5/20 min) at flow velocity 0.25 mL/min.

EXAMPLE 1

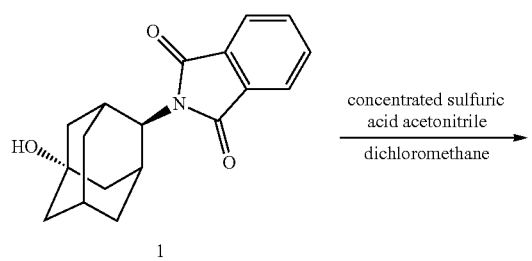

Compound 1 was synthesized according to a method described in WO2007/114125.

To dichloromethane (6 ml) and acetonitrile (3 ml) was suspended Compound 1 (1.6 g), then the reaction mixture was cooled to 0° C. To the reaction mixture was added dropwise concentrated sulfuric acid (1.1 g), then the reaction mixture was stirred at 0° C. for 20 minutes. The reaction mixture was continuously stirred at room temperature for 14 hours. After the completion of the reaction, to cooled aqueous saturated sodium hydrogen carbonate solution was added the reaction mixture, then extracted with dichloromethane. The organic layer was washed with brine and dried over sodium sulfate. The solvent was removed under reduced pressure, then the obtained residue was purified by column chromatography to give Compound 2 (1.55 g, 85.1%).

NMR (d6-DMSO); δ(ppm) 1.50-1.53 (m, 2H), 1.77 (s, 3H), 1.94-2.03 (m, 5H), 2.12-2.18 (m, 4H), 2.68 (br s, 2H), 4.19 (s, 1H), 7.39 (s, 1H), 7.82 (s, 4H).

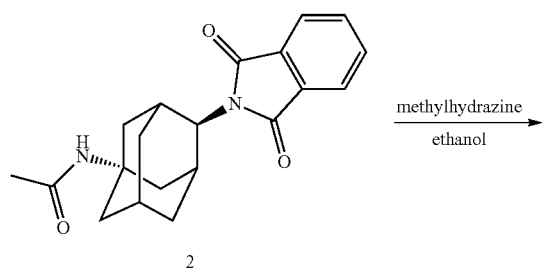

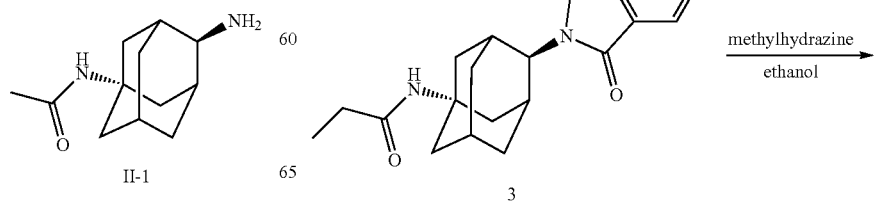

To a suspension of Compound 2 (1.55 g) in ethanol (16 ml) was added methylhydrazine (0.61 ml), the reaction mixture was refluxed for 28 hours. After the completion of the reaction, the solvent was removed under reduced pressure. To the residue were added 2N aqueous hydrochloric acid solution and ethyl acetate, then the mixture was stirred. The insoluble residue was collected by filtration, then the filtrate was separated. The aqueous layer was washed with ethyl acetate, then concentrated under reduced pressure. The residue was alkalified with 5N aqueous sodium hydroxide and extracted with dichloromethane. The organic layer was washed with brine and dried over magnesium sulfate. The solvent was removed under reduced pressure to give amine II-1.

NMR (d6-DMSO); δ(ppm) 1.24-1.28 (m, 2H), 1.69-1.99 (m, 14H), 2.86 (s, 1H), 7.25 (s, 1H)

EXAMPLE 2

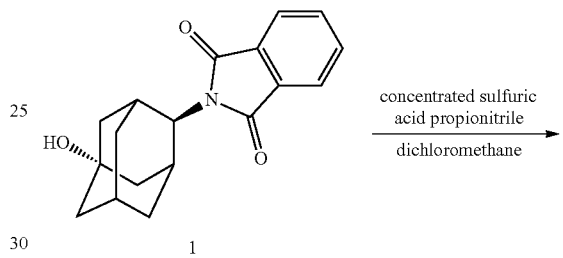

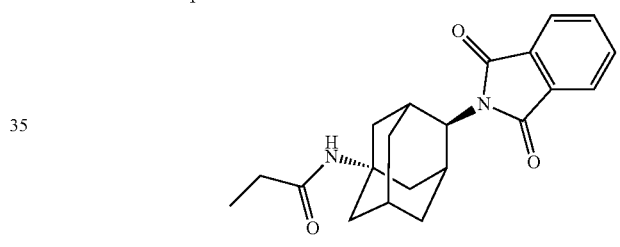

To dichloromethane (6 ml) and propionitrile (3 ml) was suspended Compound 1 (1.5 g), then the reaction mixture was cooled to 0° C. To the reaction suspension was added dropwise concentrated sulfuric acid (990 mg), then the reaction mixture was stirred at room temperature for 18 hours. After the completion of the reaction, to cooled aqueous saturated sodium hydrogen carbonate solution was added the reaction mixture, then extracted with dichloromethane. The organic layer was washed with brine and dried over sodium sulfate. The solvent was removed under reduced pressure, then the obtained residue was purified by column chromatography to give Compound 3 (1.17 g, 65.8%).

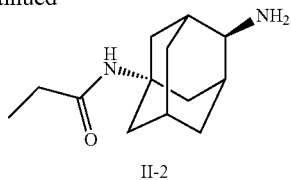

II-2

To a suspension of Compound 3 (1.17 g) in ethanol (12 ml) was added methylhydrazine (442 μl), the reaction mixture was refluxed for 24 hours. After the completion of the reaction, the solvent was removed under reduced pressure. To the residue were added 2N aqueous hydrochloric acid solution and ethyl acetate, then the mixture was stirred. The insoluble residue was collected by filtration, then the filtrate was separated. The aqueous layer was washed with ethyl acetate, then concentrated under reduced pressure. The residue was alkalified with 2N aqueous sodium hydroxide and extracted with dichloromethane. The organic layer was washed with brine and dried over magnesium sulfate. The solvent was removed under reduced pressure to give amine II-2 (660 mg, 89.4%).

NMR (d6-DMSO); δ(ppm) 0.93 (t, J=7.6 Hz, 3H), 1.25-1.28 (m, 2H), 1.69 (br s, 2H), 1.87-2.02 (m, 11H), 2.86 (s, 1H), 7.16 (s, 1H)

EXAMPLE 3

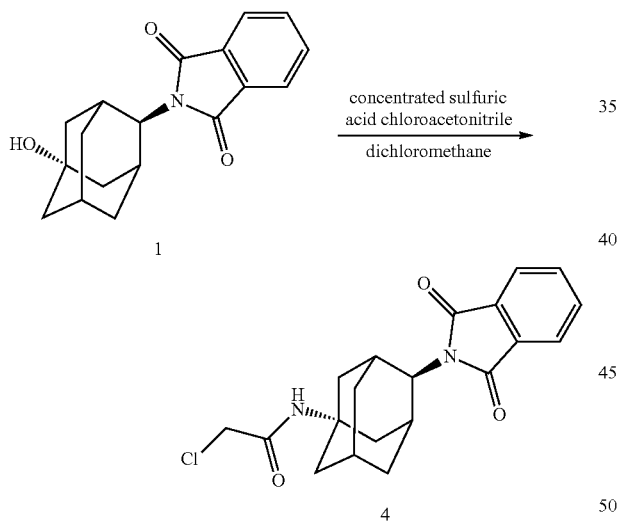

To dichloromethane (7 ml) and chloroacetonitrile (3.5 ml) was suspended Compound 1 (2.0 g), then the reaction mixture was cooled to 0° C. To the reaction mixture was added dropwise concentrated sulfuric acid (990 mg), then the reaction mixture was stirred at room temperature for 6.5 hours. After the completion of the reaction, to cooled aqueous saturated sodium hydrogen carbonate solution was added the reaction mixture, then extracted with dichloromethane. The organic layer was washed with brine and dried over sodium sulfate. The solvent was removed under reduced pressure, then the obtained residue was purified by column chromatography to give Compound 4 (2.37 g, 94.5%).

NMR (d6-DMSO); δ(ppm) 1.52-1.55 (m, 2H), 1.96-2.19 (m, 9H), 2.71 (br s, 2H), 3.98 (s, 2H), 4.20 (s, 1H), 7.77 (s, 1H), 7.82 (s, 4H)

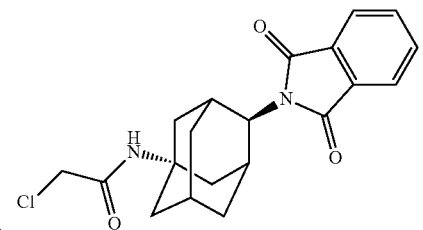

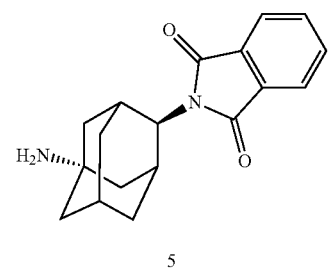

To a solution of Compound 4 (2.37 g) in ethanol (13 ml) were added acetic acid (2.6 ml) and thiourea (581 mg), the reaction mixture was refluxed for 14 hours. After the completion of the reaction, to the reaction mixture was added water. The insoluble residue was collected by filtration. The filtrate was alkalified with 5N aqueous sodium hydroxide and extracted with dichloromethane. The organic layer was washed with brine and dried over magnesium sulfate. The solvent was removed under reduced pressure to give Compound 5 (1.33 g). The obtained product was used for the next reaction without further purification.

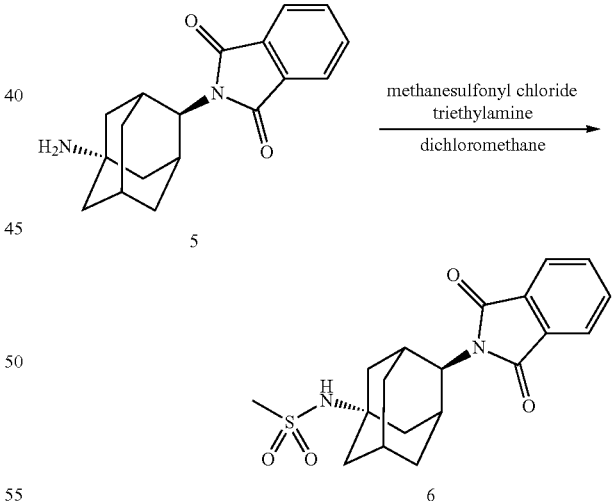

To a solution of Compound 5 (1.33 g) in dichloromethane (15 ml) was added triethylamine (1.26 ml), then the reaction mixture was cooled to 0° C. To the reaction mixture was added methanesulfonyl chloride (418 μl), then the reaction mixture was stirred at room temperature for 1.5 hours. After the completion of the reaction, the organic layer was washed with 1N aqueous hydrochloric acid solution. The solvent was removed under reduced pressure, then the obtained residue was purified by column chromatography to give Compound 6 (907 mg, 53.7%).

NMR (d6-DMSO); δ(ppm) 1.49-1.52 (m, 2H), 1.93-2.15 (m, 9H), 2.72 (br s, 2H), 3.34 (s, 3H), 4.16 (s, 1H), 6.93 (s, 1H), 7.82 (s, 4H)

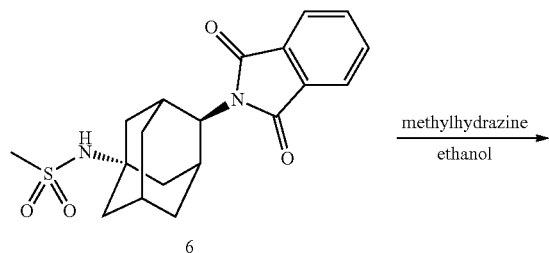

To a suspension of Compound 6 (907 mg) in ethanol (20 ml) was added methylhydrazine (322 μl), the reaction mixture was refluxed overnight. After the completion of the reaction, the solvent was removed under reduced pressure. To the residue were added 2N aqueous hydrochloric acid solution and a mixed solution (1:1) of ethyl acetate and hexane, then the mixture was stirred. The insoluble residue was collected by filtration, then the filtrate was separated. The aqueous layer was washed with ether. The aqueous layer was alkalified with 5N aqueous sodium hydroxide and extracted with dichloromethane. The organic layer was washed with brine and dried over magnesium sulfate. The solvent was removed under reduced pressure to give amine II-3 (321 mg, 54.2%).

NMR (d6-DMSO); δ(ppm) 1.23-1.26 (m, 2H), 1.71-1.99 (m, 11H), 2.84 (s, 1H), 2.92 (s, 3H), 6.76 (br s, 1H)

EXAMPLE 4

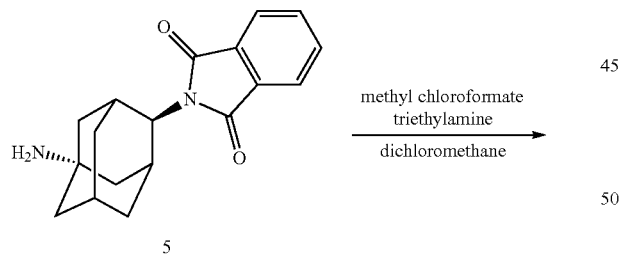

To a solution of Compound 5 (700 mg) in dichloromethane (14 ml) was added triethylamine (0.99 ml), then the reaction mixture was cooled to 0° C. To the reaction mixture was added methyl chloroformate (272 μl), then the reaction mixture was stirred at room temperature for 4 hours. After the completion of the reaction, to 0.5N aqueous hydrochloric acid solution was added the reaction mixture, then extracted with dichloromethane. The organic layer was washed with brine and dried over sodium sulfate. The solvent was removed under reduced pressure, then the obtained residue was purified by column chromatography to give Compound 7 (266 mg, 31.8%).

NMR (d6-DMSO); δ(ppm) 1.49-1.52 (m, 2H), 1.89-2.16 (m, 9H), 2.68 (br s, 2H), 3.49 (s, 3H), 4.16 (s, 1H), 6.92 (s, 1H), 7.82 (s, 4H)

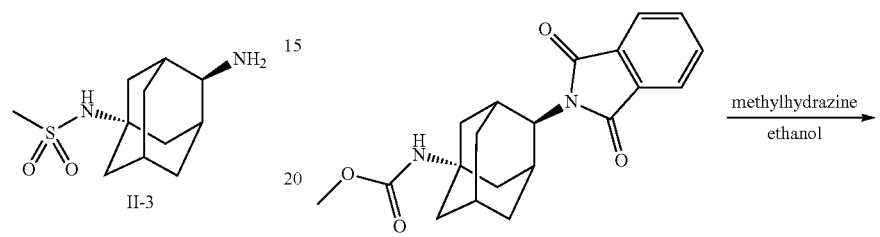

To a suspension of Compound 7 (259 mg) in ethanol (3 ml) was added methylhydrazine (97 μl), the reaction mixture was refluxed for 24 hours. After the completion of the reaction, the solvent was removed under reduced pressure. To the residue was added 2N aqueous hydrochloric acid solution. The insoluble residue was collected by filtration. The aqueous layer was washed with ethyl acetate. The aqueous layer was alkalified with 5N aqueous sodium hydroxide and extracted with dichloromethane. The organic layer was washed with brine and dried over magnesium sulfate. The solvent was removed under reduced pressure to give amine II-4 (135 mg, 82.4%).

NMR (d6-DMSO); δ(ppm) 1.23-1.26 (m, 2H), 1.69-1.99 (m, 11H), 2.84 (s, 1H), 3.45 (s, H), 6.76 (s, 1H)

EXAMPLE 5

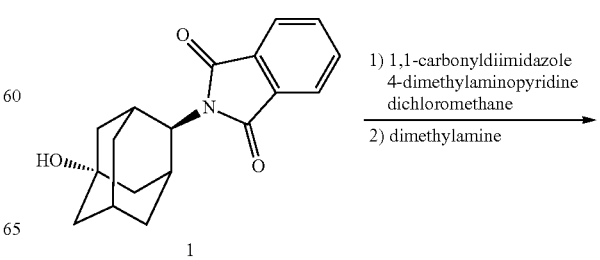

25
-continued

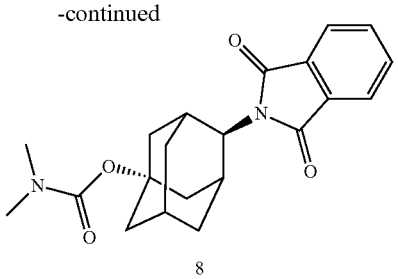

To a solution of Compound 1 (5.0 g) in dichloromethane (50 ml) were added 1,1'-carbonyldiimidazole (3.27 g) and 4'-dimethylaminopyridine (411 mg), then the reaction mixture was stirred at room temperature for 14 hours. After confirming the disappearance of the starting material, to the reaction mixture was added dimethylamine (25.2 ml, 2M tetrahydrofuran solution), then the reaction mixture was continuously stirred at room temperature for 10 hours. After the completion of the reaction, the reaction mixture was acidified with 2N aqueous hydrochloric acid solution and extracted with chloroform. The organic layer was washed with brine and dried over sodium sulfate. The solvent was removed under reduced pressure, then the obtained residue was purified by column chromatography to give Compound 8 (2.73 g, 44.1%).

NMR (d6-DMSO); δ(ppm) 1.48-1.57 (m, 2H), 2.060-2.29 (m, 9H), 2.72-2.86 (m, 8H), 4.18-4.22 (br, 1H), 7.82 (s, 4H)

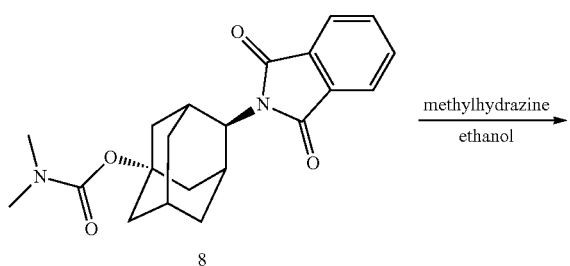

To a solution of Compound 8 (1.0 g) in ethanol (10 ml) was added methylhydrazine (361 μl), the reaction mixture was refluxed for 20 hours. After the completion of the reaction, the solvent was removed under reduced pressure. To the residue were added 2N aqueous hydrochloric acid solution and ethyl acetate. The mixture was stirred and separated. The aqueous layer was washed with ethyl acetate, then concentrated under reduced pressure. The residue was alkalified with aqueous sodium carbonate solution. The obtained solid was collected by filtration and washed with water, then dried to give amine II-5 (500 mg, 77.3%).

26

NMR (CDCl$_3$); δ(ppm) 1.42-1.51 (m, 2H), 1.88-2.19 (m, 11H), 2.85 (s, 6H), 3.05-3.10 (br, 1H)

EXAMPLE 6

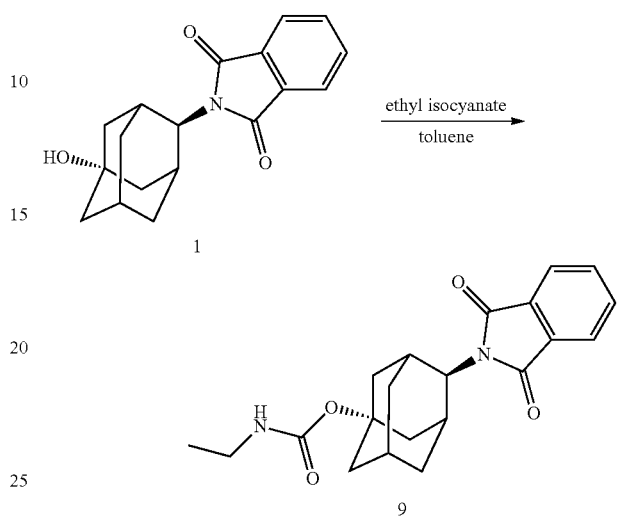

To a solution of Compound 1 (2.0 g) in toluene (20 ml) was added ethyl isocyanate (2.7 ml), the reaction mixture was refluxed for 8.5 hours. After the completion of the reaction, the solvent was removed under reduced pressure. The obtained solid was washed with diisopropyl ether, then dried to give Compound 9 (2.15 g, 86.7%).

NMR (d6-DMSO); δ(ppm) 0.99 (t, J=7.2 Hz, 3H), 1.47-1.57 (m, 2H), 2.04-2.32 (m, 9H), 2.76-2.84 (br, 2H), 2.88-3.00 (m, 2H), 4.17-4.22 (br, 1H), 6.84-6.91 (m, 1H), 7.83 (s, 4H)

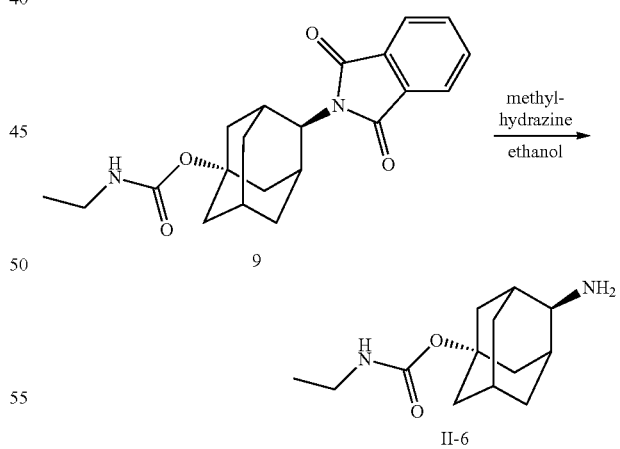

To a solution of Compound 9 (1.0 g) in ethanol (10 ml) was added methylhydrazine (361 μl), the reaction mixture was refluxed for 25 hours. After the completion of the reaction, the solvent was removed under reduced pressure. To the residue were added 2N aqueous hydrochloric acid solution and ethyl acetate. The mixture was stirred and separated. The aqueous layer was washed with ethyl acetate, then concentrated under reduced pressure. The residue was alkalified with aqueous sodium carbonate solution and extracted with chloroform.

The organic layer was washed with brine and dried over sodium sulfate. The solvent was removed under reduced pressure. The obtained residue was washed with diisopropyl ether, then dried to give amine II-6 (475 mg, 73.4%).

NMR (CDCl$_3$); δ(ppm) 1.11 (t, J=7.2 Hz, 3H), 1.38-1.51 (m, 2H), 1.87-2.18 (m, 11H), 3.03-3.21 (m, 3H), 4.42-4.59 (br, 1H)

EXAMPLE 7

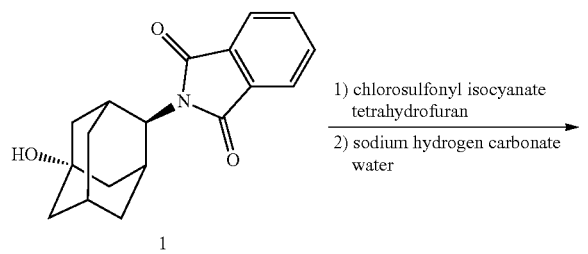

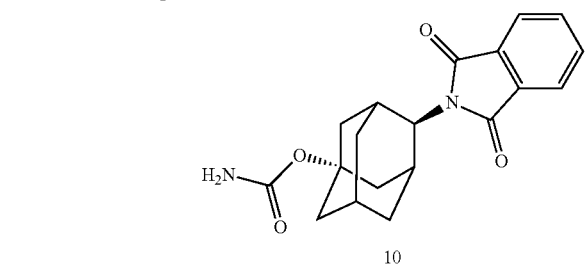

A solution of Compound 1 (2.5 g) in tetrahydrofuran (50 ml) was cooled to −30° C. To the solution was added chlorosulfonyl isocyanate (1.5 ml), then the reaction mixture was stirred at −30° C. for one hour. To the reaction mixture were added sodium hydrogen carbonate (3.5 g) and water (1 ml), then the reaction mixture was stirred at room temperature for 16 hours. The reaction mixture was extracted with chloroform. The organic layer was washed with brine and dried over sodium sulfate. The solvent was removed under reduced pressure. The obtained residue was washed with diisopropyl ether, then dried to give Compound 10 (2.73 g, 95.5%).

NMR (d6-DMSO); δ(ppm) 1.46-1.58 (m, 2H), 2.02-2.30 (m, 9H), 2.76-2.84 (br, 2H), 4.16-4.22 (br, 1H), 6.10-6.35 (m, 1H), 7.82 (s, 4H)

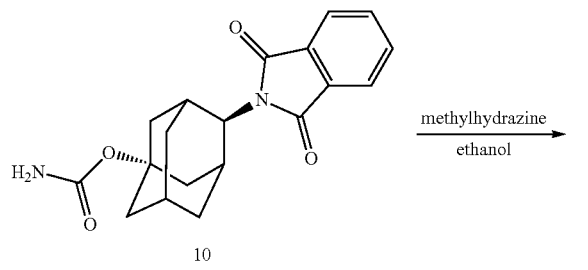

To a solution of Compound 10 (1.0 g) in ethanol (10 ml) was added methylhydrazine (391 μl), the reaction mixture was refluxed for 21 hours. After the completion of the reaction, the solvent was removed under reduced pressure. To the residue were added 2N aqueous hydrochloric acid solution and ethyl acetate. The mixture was stirred and separated. The aqueous layer was washed with ethyl acetate, then concentrated under reduced pressure. The residue was alkalified with aqueous sodium carbonate solution. The obtained solid was collected by filtration and washed with water, then dried to give amine II-7 (468 mg, 75.7%).

NMR (d6-DMSO); δ(ppm) 1.40-1.51 (m, 2H), 1.91-2.22 (m, 11H), 3.28-3.34 (br, 1H), 6.06-6.42 (br, 2H), 8.08-8.34 (br, 2H)

EXAMPLE 8

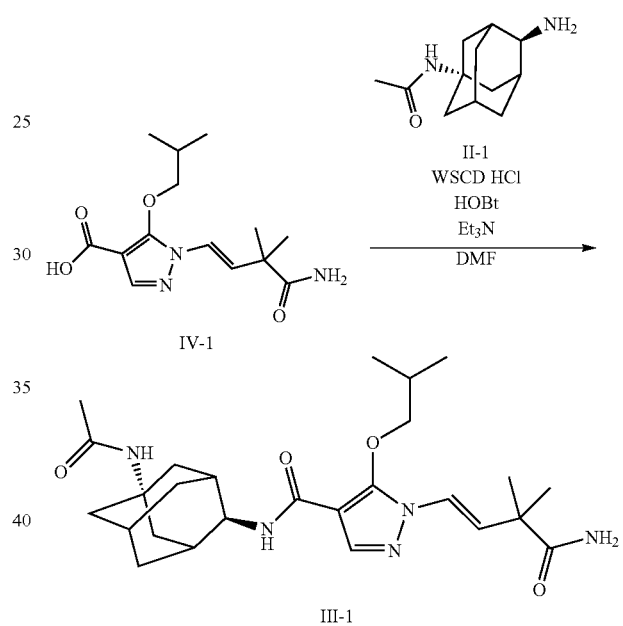

Compound IV-1 was synthesized by hydrolyzing Compound 33 of Example 32 described in WO2007/058346 under alkaline condition.

To a solution of Compound IV-1 (300 mg) in dimethylformamide (6.0 ml) were added amine II-1 (254 mg), 1-(3-dimethylaminopropyl)-3-ethylcarbodiimide hydrochloride (WSCD HCl) (254 mg), 1-hydroxybenzotriazole (HOBt) (41 mg) and triethylamine (212 μl), then the reaction mixture was stirred at room temperature for 14 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound III-1 (244 mg, 49.5%).

NMR (d6-DMSO);

δ(ppm) 0.98 (d, J=6.8 Hz, 6H), 1.27 (s, 6H), 1.42 (d, J=12.4 Hz, 2H), 1.75 (s, 3H), 1.93-2.03 (m, 12H), 3.93 (brs, 1H), 4.10 (d, J=6.4 Hz, 2H), 6.37 (d, J=14.4 Hz, 1H), 6.81 (d, J=14.0 Hz, 1H), 6.92 (brs, 1H), 7.14 (brs, 1H), 7.35 (s, 1H), 7.41 (d, J=6.4 Hz, 1H), 7.98 (s, 1H)

EXAMPLE 9

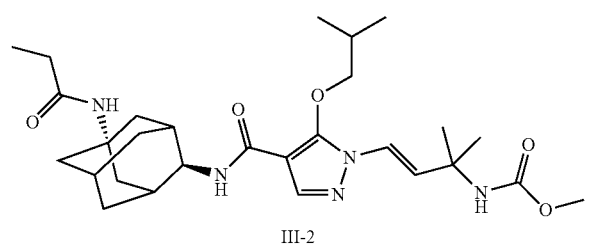

Compound IV-2 was synthesized by hydrolyzing CO$_2$tBu group of Compound 20 of Example 29 described in WO2007/058346 under acidic condition to give carboxylic acid, converting the obtained carboxylic acid to isocyanate using DPPA/Et$_3$N, reacting the obtained isocyanate with methanol, then hydrolyzing CO$_2$Et group under alkali condition. DPPA is diphenylphosphoryl azide.

To a solution of Compound IV-2 (100 mg) in dimethylformamide (2.0 ml) were added amine II-2 (82 mg), 1-(3-dimethylaminopropyl)-3-ethylcarbodiimide hydrochloride (88 mg), 1-hydroxybenzotriazole (12 mg) and triethylamine (86 μl), then the reaction mixture was stirred at room temperature overnight. After the completion of the reaction, to 0.5N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound III-2 (145 mg, 89.0%).

log k'=0.909

EXAMPLE 10

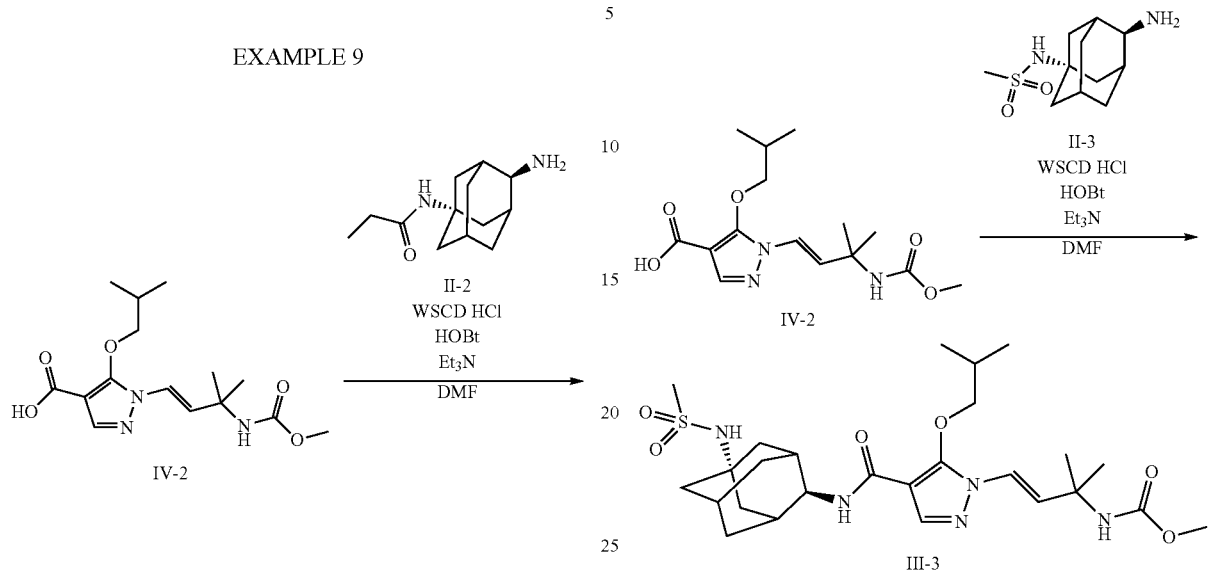

To a solution of Compound IV-2 (200 mg) in dimethylformamide (4.0 ml) were added amine II-3 (151 mg), 1-(3-dimethylaminopropyl)-3-ethylcarbodiimide hydrochloride (153 mg), 1-hydroxybenzotriazole (25 mg) and triethylamine (128 μl), then the reaction mixture was stirred at room temperature for 3 days. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound III-3 (310 mg, 91.4%).

NMR (d6-DMSO); δ(ppm) 0.97 (d, J=6.4 Hz, 6H), 1.38-1.42 (m, 8H), 1.89-2.05 (m, 12H), 2.92 (s, 3H), 3.49 (s, 3H), 3.91 (brs, 1H), 4.08 (d, J=6.4 Hz, 2H), 6.30 (d, J=14.4 Hz, 1H), 6.79 (d, J=14.0 Hz, 1H), 6.87 (s, 1H), 7.25 (s, 1H), 7.44 (d, J=6.0 Hz, 1H), 7.96 (s, 1H)

EXAMPLE 11

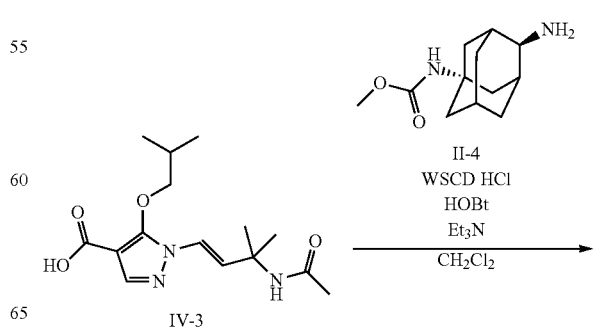

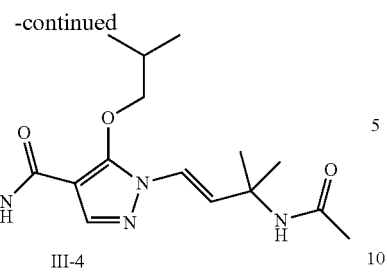

III-4

Compound IV-3 is Compound 29 of Example 30 described in WO2007/058346.

To a solution of Compound IV-3 (80 mg) in dichloromethane (2.0 ml) were added amine II-4 (64 mg), 1-(3-dimethylaminopropyl)-3-ethylcarbodiimide hydrochloride (65 mg), 1-hydroxybenzotriazole (11 mg) and triethylamine (54 μl), then the reaction mixture was stirred at room temperature overnight. After the completion of the reaction, to 0.5N aqueous hydrochloric acid solution was added the reaction mixture, then extracted with dichloromethane. The organic layer was washed respectively with saturated sodium bicarbonate solution and brine, then dried over sodium sulfate. The solvent was removed under reduced pressure. The obtained residue was purified by column chromatography to give Compound III-4 (100 mg, 75.0%).

log k'=0.886

EXAMPLE 12

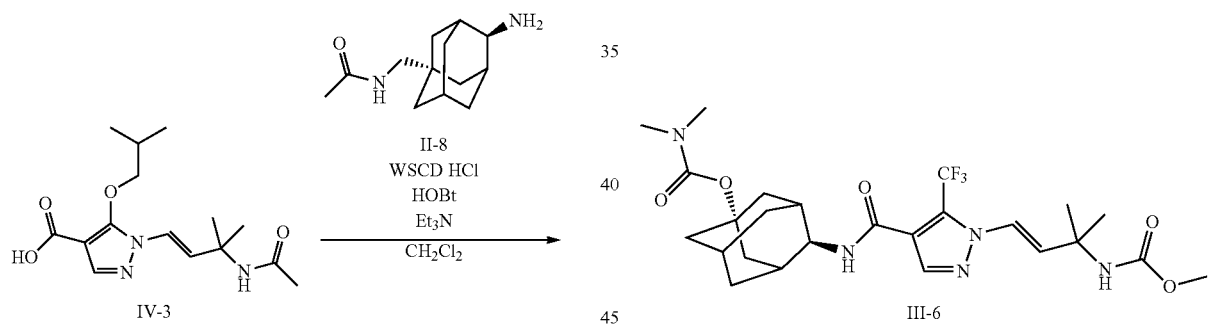

IV-3

III-5

To a solution of Compound IV-3 (80 mg) in dichloromethane (3.2 ml) were added amine II-8 (74 mg), 1-(3-dimethylaminopropyl)-3-ethylcarbodiimide hydrochloride (WSCD) (65 mg), 1-hydroxybenzotriazole (HOBt) (11 mg) and triethylamine (90 μl), then the reaction mixture was stirred at room temperature for 36 hours. After the completion of the reaction, to 0.5N aqueous hydrochloric acid solution was added the reaction mixture, then extracted with dichloromethane. The organic layer was washed respectively with saturated sodium bicarbonate solution and brine, then dried over sodium sulfate. The solvent was removed under reduced pressure. The obtained residue was purified by column chromatography to give Compound III-5 (98 mg, 73.8%).

log k'=0.838

EXAMPLE 13

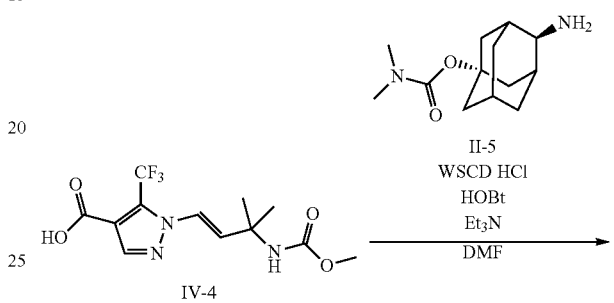

IV-4

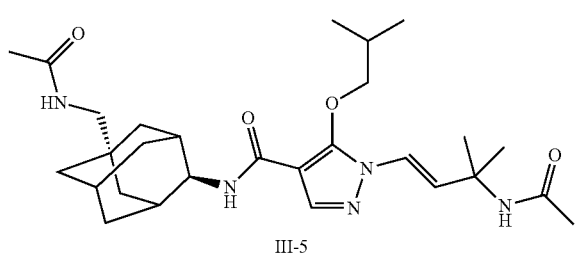

III-6

Compound IV-4 is Compound II-18 of Example 84 described in WO2008/142986.

To a solution of Compound IV-14 (100 mg) in dimethylformamide (2.0 ml) were added amine II-5 (89 mg), 1-(3-dimethylaminopropyl)-3-ethylcarbodiimide hydrochloride (78 mg), 1-hydroxybenzotriazole (12.6 mg) and triethylamine (108 μl), then the reaction mixture was stirred at room temperature for 23 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound III-6 (155 mg, 91.7%).

NMR (d6-DMSO); δ(ppm) 1.40 (s, 8H), 1.88-2.14 (m, 11H), 2.77 (s, 6H), 3.49 (s, 3H), 3.93-4.00 (m, 1H), 6.57 (d, J=13.8 Hz, 1H), 6.88 (d, J=13.8 Hz, 1H), 7.36 (s, 1H), 7.96 (s, 1H), 8.34 (d, J=7.2 Hz, 1H)

EXAMPLE 14

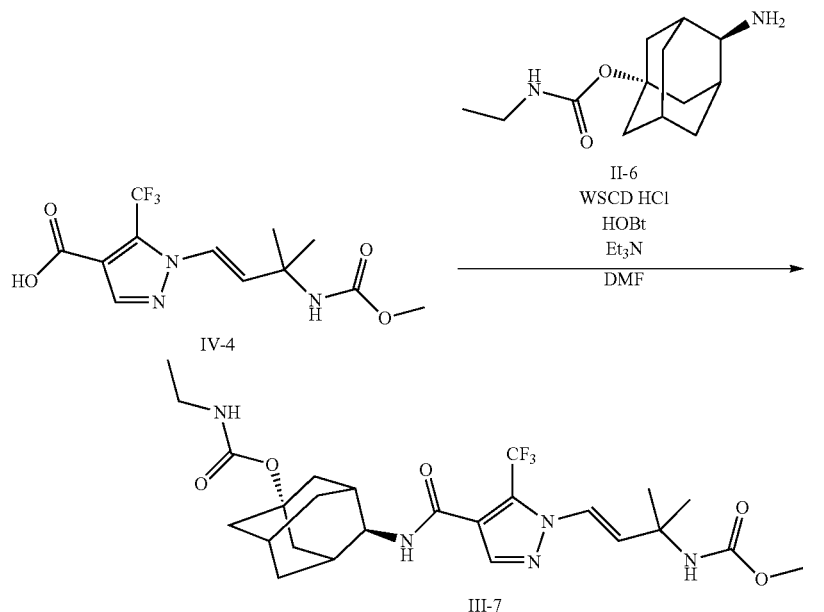

To a solution of Compound IV-4 (100 mg) in dimethylformamide (2.0 ml) were added amine II-6 (89 mg), 1-(3-dimethylaminopropyl)-3-ethylcarbodiimide hydrochloride (78 mg), 1-hydroxybenzotriazole (12.6 mg) and triethylamine (108 μl), then the reaction mixture was stirred at room temperature for 20 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound III-7 (122 mg, 72.2%).

NMR (d6-DMSO); δ(ppm) 0.98 (t, J=6.9 Hz, 3H), 1.40 (s, 8H), 1.88-2.13 (m, 11H), 2.88-2.97 (m, 2H), 3.49 (s, 3H), 3.93-3.99 (m, 1H), 6.57 (d, J=13.8 Hz, 1H), 6.81-6.92 (m, 2H), 7.34 (s, 1H), 7.96 (s, 1H), 8.33 (d, J=6.6 Hz, 1H)

EXAMPLE 15

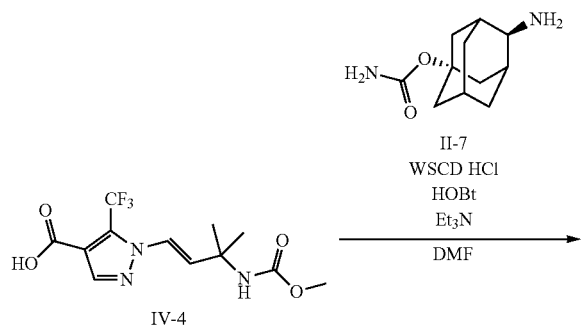

-continued

To a solution of Compound IV-4 (100 mg) in dimethylformamide (2.0 ml) were added amine II-7 (79 mg), 1-(3-dimethylaminopropyl)-3-ethylcarbodiimide hydrochloride (78 mg), 1-hydroxybenzotriazole (12.6 mg) and triethylamine (108 μl), then the reaction mixture was stirred at room temperature for 14 hours. After the completion of the reaction, to 2N aqueous hydrochloric acid solution was added the reaction mixture, then extracted with ethyl acetate. The organic layer was washed respectively with saturated sodium bicarbonate solution and brine, then dried over sodium sulfate. The solvent was removed under reduced pressure. The obtained residue was purified by column chromatography to give Compound III-8 (137 mg, 85.6%).

NMR (d6-DMSO); δ(ppm) 1.40 (s, 8H), 1.88-2.13 (m, 11H), 3.50 (s, 3H), 3.94-3.99 (m, 1H), 6.05-6.35 (s, 2H), 6.58 (d, J=13.6 Hz, 1H), 6.88 (d, J=13.6 Hz, 1H), 7.35 (s, 1H), 7.96 (s, 1H), 8.33 (d, J=6.8 Hz, 1H)

INDUSTRIAL APPLICABILITY

A compound represented by the formula (II) is useful as an intermediate for producing a compound represented by the formula (III). A compound represented by the formula (III) can be produced effectively by using an intermediate of the present invention.

The invention claimed is:

1. A compound represented by the formula (II):

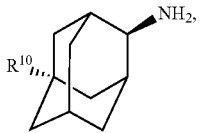

its salt, or a solvate thereof,
wherein
R$^{10}$ is a group represented by the formula: —(CR$^{13}$R$^{14}$)m-O—C(O)—NR$^{15}$—R$^{16}$,
wherein R$^{13}$ and R$^{14}$ are each independently hydrogen, substituted or unsubstituted alkyl or halogen, m is an integer of 0 to 3, and R$^{15}$ and R$^{16}$ are each independently hydrogen or substituted or unsubstituted alkyl.

2. The compound according to claim 1, its salt, or a solvate thereof, wherein m is 0.

3. A process for producing a compound represented by the formula (III):

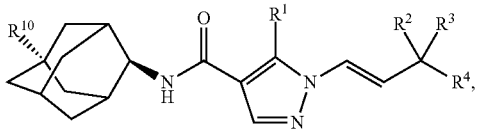

its salt, or a solvate thereof,
wherein
R$^1$ is a group represented by the formula: —Y—R$^5$,
wherein Y is a bond, —O— or —S—, R$^5$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl or substituted or unsubstituted heterocyclyl,
R$^2$ and R$^3$ are each independently hydrogen, substituted or unsubstituted alkyl or halogen, or R$^2$ and R$^3$ taken together with the adjacent carbon atom to which they are attached may form a substituted or unsubstituted ring,
R$^4$ is a group represented by the formula: —C(=O)—NR$^6$R$^7$,
wherein R$^6$ and R$^7$ are each independently hydrogen, substituted or unsubstituted amino, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted alkylsulfonyl, substituted or unsubstituted arylsulfonyl, substituted or unsubstituted heteroarylsulfonyl or substituted or unsubstituted heterocyclylsulfonyl, R$^6$ and R$^7$ taken together with the adjacent nitrogen atom to which they are attached may form a substituted or unsubstituted ring or
a group represented by the formula: —NR$^8$R$^9$,
wherein R$^8$ and R$^9$ are each independently hydrogen, carboxy, hydroxy, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, substituted or unsubstituted acyl, substituted or unsubstituted carbamoyl, substituted or unsubstituted thiocarbamoyl, substituted or unsubstituted alkylsulfonyl, substituted or unsubstituted arylsulfonyl, substituted or unsubstituted alkyloxycarbonyl or substituted or unsubstituted sulfamoyl, R$^8$ and R$^9$ taken together with the adjacent nitrogen atom to which they are attached may form a substituted or unsubstituted ring, R$^{10}$ is as defined in claim 1,
which comprises reacting a compound represented by the formula (I):

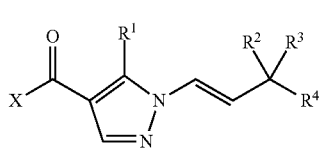

wherein R$^1$, R$^2$, R$^3$ and R$^4$ are as defined above, X is hydroxy or a leaving group, and a compound represented by the formula (II):

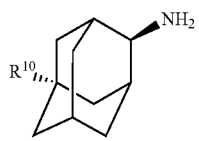

wherein R$^{10}$ is as defined in claim 1.

4. The process according to claim 3, wherein X is hydroxy and the reaction is performed in the presence of a condensing agent.

5. The process according to claim 4, wherein the condensing agent is one or more condensing agent(s) selected from N,N'-dicyclohexylcarbodiimide, N,N'-diisopropylcarbodiimide and 1-ethyl-3-(3-dimethylamino propyl)carbodiimide hydrochloride.

6. The process according to claim 4, wherein the reaction is performed in the presence of one or more additive agent(s) selected from 1-hydroxybenzotriazole and N-hydroxy succinimide.

7. The process according to claim 3, which includes a step of obtaining the compound represented by the formula (I):

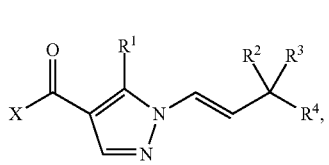

its salt, or a solvate thereof,
wherein
X is halogen, R$^1$, R$^2$, R$^3$ and R$^4$ are as defined in claim 3 which comprises reacting a compound represented by the formula (IV):

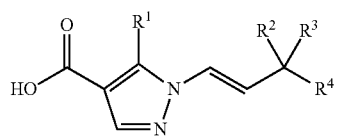

(IV)

wherein R¹, R², R³ and R⁴ are as defined in claim 3 with a halogenating agent.

8. The process according to claim 7, wherein the halogenating agent is selected from phosphorus oxychloride, phosphorus pentachloride, oxalyl chloride and thionyl chloride.

9. The process according to claim 3, which comprises reacting a compound represented by the formula (I) with a compound represented by the formula (II) in the presence of a base.

* * * * *